(12) United States Patent
Angelsen et al.

(10) Patent No.: US 7,691,060 B2
(45) Date of Patent: Apr. 6, 2010

(54) PROBE FOR 3-DIMENSIONAL SCANNING AND FOCUSING OF AN ULTRASOUND BEAM

(76) Inventors: Bjørn A. J. Angelsen, Bugges veg 4b, Trondheim (NO) N-7051; Tonni F. Johansen, Nnils Uhlin Hansens veg 50C, Trondheim (NO) N-7026

( * ) Notice: Subject to any disclaimer, the term of this patent is extended or adjusted under 35 U.S.C. 154(b) by 885 days.

(21) Appl. No.: 10/963,464

(22) Filed: Oct. 12, 2004

(65) Prior Publication Data

US 2005/0119572 A1    Jun. 2, 2005

Related U.S. Application Data

(60) Provisional application No. 60/510,208, filed on Oct. 10, 2003.

(51) Int. Cl.
*A61B 8/00* (2006.01)
*A61B 8/14* (2006.01)

(52) U.S. Cl. .................. 600/443; 600/447; 600/462

(58) Field of Classification Search ............... 600/443, 600/445, 447, 444, 459, 462; 367/103
See application file for complete search history.

(56) References Cited

U.S. PATENT DOCUMENTS

| | | | | |
|---|---|---|---|---|
| 5,152,294 A | * | 10/1992 | Mochizuki et al. | 600/459 |
| 5,195,519 A | * | 3/1993 | Angelsen | 600/454 |
| 6,290,648 B1 | * | 9/2001 | Kamiyama | 600/443 |
| 6,309,353 B1 | * | 10/2001 | Cheng et al. | 600/437 |
| 6,315,724 B1 | * | 11/2001 | Berman et al. | 600/443 |
| 6,622,562 B2 | * | 9/2003 | Angelsen et al. | 73/633 |
| 6,679,849 B2 | * | 1/2004 | Miller et al. | 600/463 |
| 6,709,397 B2 | * | 3/2004 | Taylor | 600/459 |
| 6,780,153 B2 | * | 8/2004 | Angelsen et al. | 600/444 |
| 2001/0034484 A1 | * | 10/2001 | Nakamura et al. | 600/443 |
| 2002/0139193 A1 | * | 10/2002 | Angelsen et al. | 73/602 |
| 2003/0018269 A1 | * | 1/2003 | Angelsen et al. | 600/459 |
| 2003/0163046 A1 | * | 8/2003 | Nohara et al. | 600/443 |
| 2004/0106869 A1 | * | 6/2004 | Tepper | 600/443 |

* cited by examiner

*Primary Examiner*—Eric F Winakur
*Assistant Examiner*—Katherine L Fernandez
(74) *Attorney, Agent, or Firm*—Cohen Pontani Lieberman & Pavane LLP

(57) ABSTRACT

An ultrasound probe for three-dimensional scanning and focusing of an ultrasound beam in both an azimuth direction and an elevation direction normal to the azimuth direction. The probe is composed of an ultrasound transducer array which has a linear division of the elements in the azimuth direction for electronic steering of the beam direction and focus in the azimuth direction. The array elements have a coarse division in the elevation direction for electronic steering of the focus in the elevation direction, and possibly small angle direction steering of the beam in the elevation direction for parallel receive and/or transmit beams. Large angle direction scanning of the beam in the elevation direction is obtained by mechanical rotation of the array around an axis. The invention implies useful embodiments for insertion of the probe into the body, through mounting the array at the distal tip of an elongated device.

18 Claims, 4 Drawing Sheets

PROBE FOR 3-DIMENSIONAL SCANNING AND FOCUSING OF AN ULTRASOUND BEAM

RELATED APPLICATIONS

This application claims priority from U.S. Provisional Patent Application Ser. No. 60/510,208 which was filed on Oct. 10, 2003.

BACKGROUND OF THE INVENTION

1. Field of the Invention

The present invention is directed to technology and methods for scanning and focusing an ultrasound beam in a free direction within a region of 3D space. The technology has particular applications within 3D medical ultrasound imaging, but also has applications in other areas of 3D ultrasound imaging.

2. Description of the Related Art

Three-dimensional (3D) ultrasound imaging is obtained by scanning a pulsed ultrasound beam in two side-wards directions to the beam axis. Time of flight conversion gives the image resolution along the beam direction (range), while image resolution transverse to the beam direction is obtained by the side-wards scanning of the focused beam.

With 3D imaging one can collect volume ultrasound data from the whole object so that one through computer processing can visualize any cross section of the object. This enables selection of the best 2D image planes for the diagnosis, for example showing a sagittal plane of a fetus where the location of the fetus in relation to the probe complicates direct 2D imaging of the sagittal plane.

Such 3D imaging is of particular interest when imaging from an endoluminal channel with limited ability to move the probe in relation to the object. Typical examples are transvaginal imaging of the fetus, trans-rectal imaging of the prostate, imaging during minimal invasive surgery, etc. The method is also interesting for trans-cutaneous imaging to visualize 2D image planes with an angle to the beam directions.

For adequate imaging of the object in freely selected planes or sections in a 3D volume data set, it is important that the ultrasound beam is well focused in all directions around the beam axis, as one wants to observe the object from any direction (perspective), and small objects can be interrogated with a variety of beam directions. In addition, one can want to transmit a wide beam that covers several parallel and well focused receive beams to obtain fast volume data collection with high spatial resolution of the object. In the same way one can want to transmit several beams in different directions in parallel to further reduce the time of volume data collection from the object.

There exists in the market 3D ultrasound probes based on a 2D scanning linear array (switched linear and curve linear as well as linear phased arrays), where the second direction scanning is obtained by mechanical tilting of the 2D scan plane. The scan direction in the 2D scan plane is referred to as the azimuth direction, while the direction normal to the 2D scan plane is referred to as the elevation direction. These 3D probes in the market provide electronic steering of the focus in the azimuth direction to any depth, while the focus in the elevation direction is fixed, which is a drawback with viewing planes at an angle to the beam directions.

For electronic steered focusing of the beam in both the azimuth and elevation directions, one can either use an annular array, or divide the elements of a linear array in the elevation direction for electronic focusing in the elevation direction. The linear array has an advantage over the annular array in that one can rapidly produce large changes in azimuth the beam direction, which is an advantage for Doppler imaging of low blood velocities and velocity and strain rate of moving tissue. The linear array also allows parallel transmit and receive beams in different directions, which can be used to speed up the volume data collection rate to obtain real time 3D imaging, what is commonly referred to as 4D imaging.

For large angle electronic steering of the beam direction in 3D space, the element width must be small (~$\lambda$/2, where $\lambda$ is the ultrasound wave length) both in the azimuth and the elevation directions. This produces a large number of elements (>~3000) which complicates the electronic connection to the elements and the electronic steering of the elements, requiring large space for electronics and cables that is difficult to obtain with the narrow channels available for endo-luminal probes.

SUMMARY OF THE INVENTION

The present invention provides a solution to these challenges for 3D direction scanning and focusing of an ultrasound beam, using linear phased or switched arrays for focusing and direction steering of the ultrasound beam in an azimuth 2D scan plane. For direction steering of the beam in the elevation direction at right angle to the 2D azimuth plane, the array is mechanically rotated around an axis in the extended plane which includes the 2D azimuth plane. For focusing of the ultrasound image beam in the elevation direction at all depths in the elevation direction, the invention provides two solution:

1. In the first embodiment, the linear array is given a coarse division of the elements in the elevation direction which allows electronically steered focusing in the elevation directions. While the volume direction scanning of the beam in the elevation direction is obtained by rotating the array around an axis, this embodiment according to the invention makes it possible to do small angle steering of the beam in the elevation direction for parallel receive beams in the elevation direction to improve the volume frame rate.

2. When the image object has limited movement velocities, one can use a method of synthetic focusing of the image beam in the elevation direction. With this second method, the final image beam for an azimuth coordinate is obtained through a linear combination (filtering) of the the RF-signals from several receive beams for neighboring elevation coordinates of receive beams and with same, said azimuth coordinate.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

Figure 1:
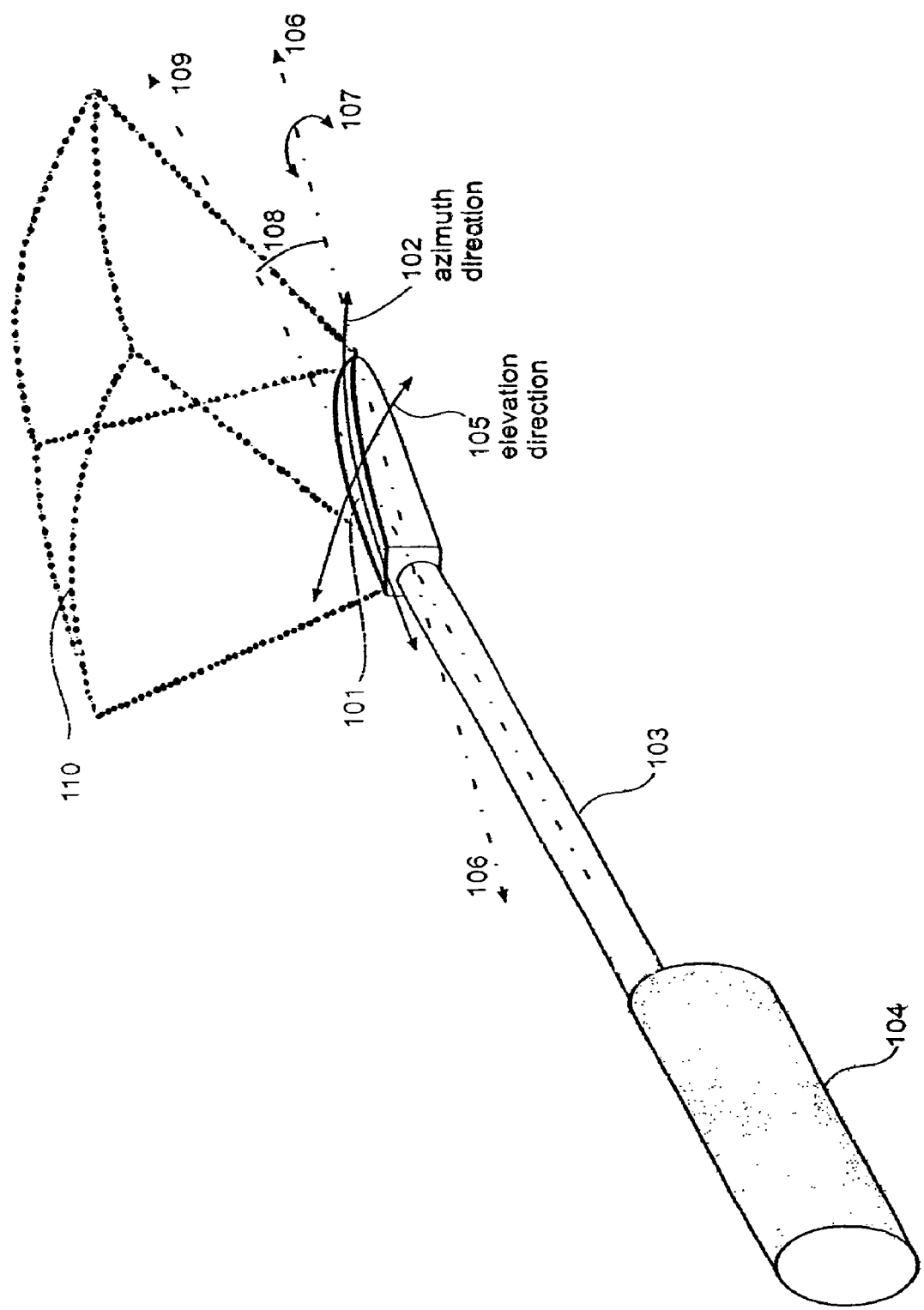
FIG. 1 shows a particular embodiment of a 3D ultrasound probe according to the invention with an ultrasound array at the tip of an elongated device for insertion into the body.

A particular embodiment according to the invention is visualized in FIG. 1. In this Figure 101 shows a linear array that is slightly convex curved in the azimuth direction 102. The array is mounted to the distal end of an elongated device 103 for insertion into the body through a channel such as the vagina, the rectum, or a minimal invasive surgery trocar. A handle 104 allows for easy manipulation of the probe and its direction.

The array 101 is designed for electronic depth steering of the focus along the beam direction both in the azimuth, 102, and elevation, 105, directions. The beam direction is electronically steered in the azimuth direction 102, while large angle beam direction steering in the elevation direction is obtained through mechanical rotation of the array around the axis 106 as indicated by the arrows 107. The rotation can for example be furthered by a motor in the elongated device 103 or in the handle 104. The array can be mounted to a stiff shaft that runs along the elongated device 103 which gives a rotation axis 106 along the axis 109 of said elongated device. The elevation rotation axis 106 can also have an angle 108 to the main axis 109 using a flexible rotation drive axis, a cardan shaft, or an angled gear. Through this combined azimuth and elevation steering of the beam direction, one is able to collect ultrasound scatter data from a volume where 110 indicates typical boundaries of such a volume.

Figure 2:
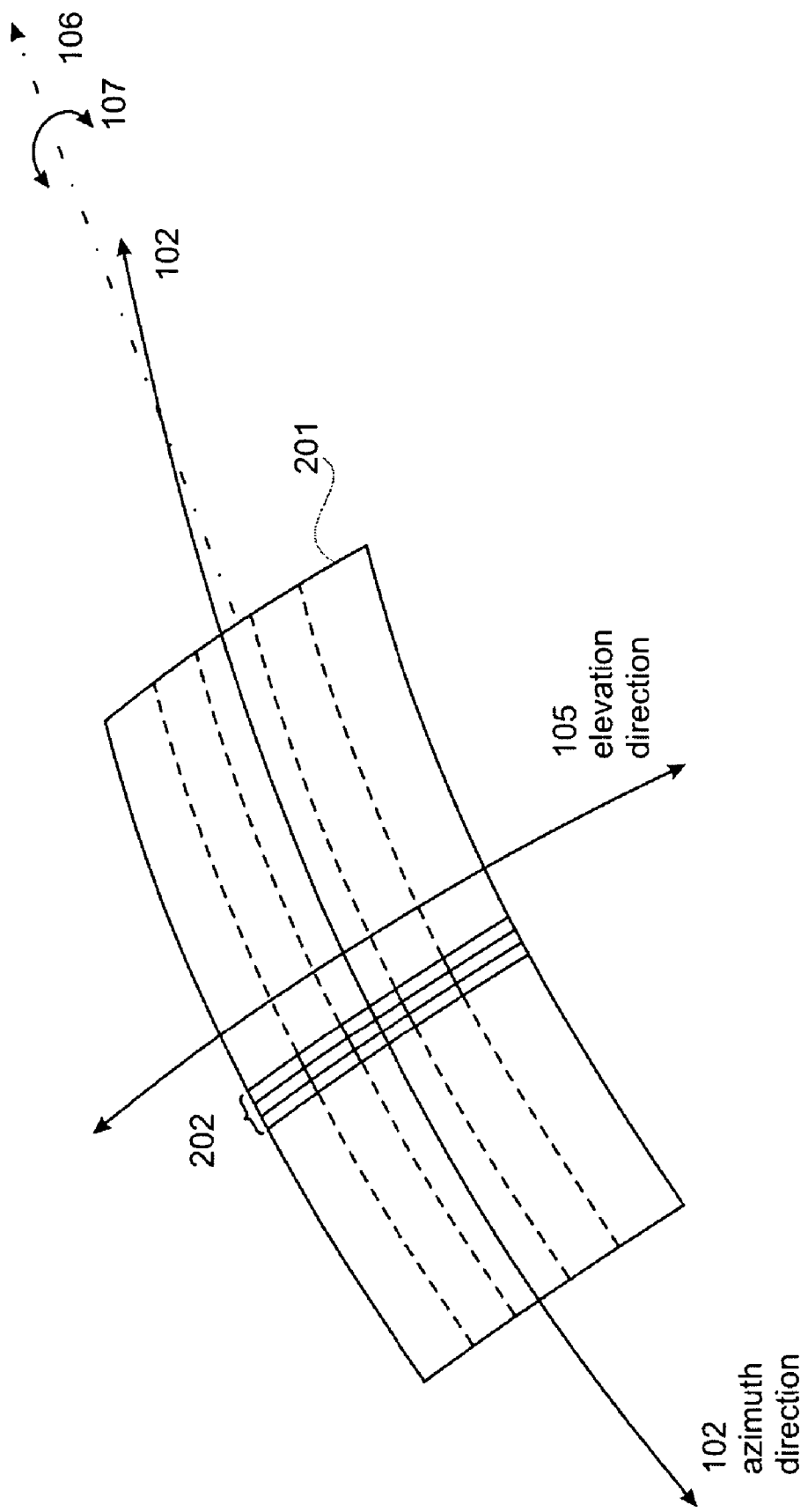
FIG. 2 shows an embodiment of an array according to the invention with a two-dimensional distribution of elements according to the invention, for electronic beam steering and focusing in the azimuth direction, and electronic focusing and small angle direction steering in the elevation direction.

Details of an example array are shown in FIG. 2, where 201 shows the array radiating surface and 202 shows a few example array elements in more detail. The array elements have a coarse division in the elevation direction compared to the azimuth direction, as the elevation division of the elements is only used for electronic depth steering of focus and possibly small angular direction steering for parallel beams in the elevation direction, while the main elevation steering of the beam is done by mechanical rotation of the array around the axis 106, indicated by the arrows 107. The elevation width of the elements must be small to give such wide element beams that the element beams that participates to an active aperture at any depth, overlaps each other. This requires that the phase error across the elements of the front of a wave from the steered focus, is limited as described below.

Hence, the array in FIG. 2 allows for electronic steered focus of the beam both in the elevation and the azimuth directions, where the beam is electronically scanned in the azimuth direction. The major volume scanning of the beam in the elevation direction is obtained through rotation of the array around the axis 106 as described above, while possible small angle elevation direction steering of the beam for parallel beams can be obtained electronically.

In the azimuth direction one needs a finer division of the elements for direction scanning of the beam, where large angle (~30-60 deg) phased array scanning requires an azimuth pitch of $\lambda/2$, while lateral beam steering with less opening angle through switching of the active group of elements in the azimuth direction of a linear or curve linear array usually allows $\lambda$-1.5$\lambda$ pitch in the azimuth direction. A preferred embodiment is a slightly convex curvature (radius of curvature ~100-600 $\lambda$) of the array in the azimuth direction with switched selection of the active elements for scanning in the azimuth direction with element azimuth pitch of k-1.5$\lambda$, as illustrated in FIGS. 1 and 2. This gives the widest aperture for a given number of elements/channels in the aperture. For large angle scanning in the azimuth direction, tightly curved arrays (radius of curvature ~50-100 $\lambda$) have commonly been used, but such geometries limits the active aperture since the difference between element direction angles increases too much with their distance. In such situations, phased array direction steering from a less curved aperture, will with an element pitch ~$\lambda/2$ provide wider apertures for a total scanning angle of ~90 deg.

FIG. 3a illustrates a typical method of focusing in the elevation direction according to the invention, where 301 shows a cross section to the azimuth direction of the array with a set of 9 elevation elements 302 for this selected azimuth position. The elements are connected to an elevation beam former unit 303, where one such unit is used for each group of elevation elements in the azimuth direction. The elevation beam former unit typically selects the group of elevation elements that participates to the beam at any depth, and possibly delays the element signals before they are added to a common signal for each azimuth group of elements at a particular depth (for transmit) or an elevation focus that follows the origin of the back scattered signal in a receive dynamic focusing mode. A typical elevation form of the beam profile as a function of depth is indicated as 304. For this profile the number of elevation elements that participates in the active aperture is expanded at the depth locations 305 and 306 to limit the diffraction expansion of the focused beam (dynamic, expanding aperture). The outputs of the elevation beam formers 303 are fed to an azimuth beam former 307 that selects and delays the signals from the whole group of elevation beam formers to add the selected signals to form the composite RF signal with electronically steered focus for a particular azimuth direction. The azimuth beam former can also output several parallel beams with small angle difference to increase the speed of data collection with high lateral azimuth resolution.

The elevation beam-former can both be used for an electronic steering of the elevation focus depth, and possibly a small angle steering of the elevation beam direction to provide parallel beams in the elevation direction. In such a situation, one can reduce the maximally required delays for elevation focusing by pre-focusing the elements in the elevation direction, for example by curving the array as 401 in FIG. 4a, or with a lens 402 on top of the array as in FIG. 4b.

Figure 3:
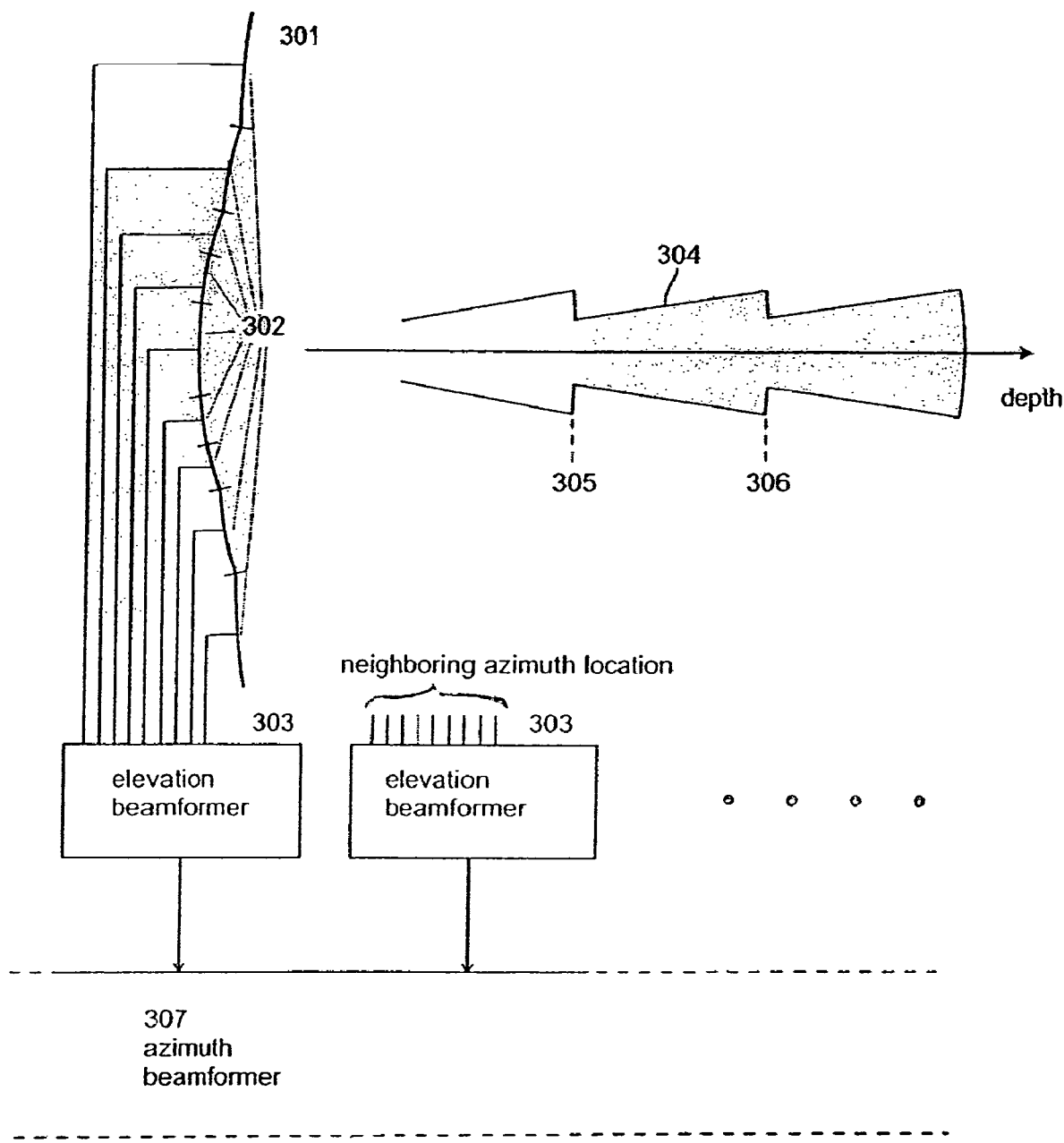
FIG. 3 shows a block diagram of beam forming structures for electronic steering of the beam focus and direction in the azimuth direction, and electronic focusing in the elevation direction with possible small angular direction steering in the elevation direction for parallel beams in the elevation direction.
Figure 4:
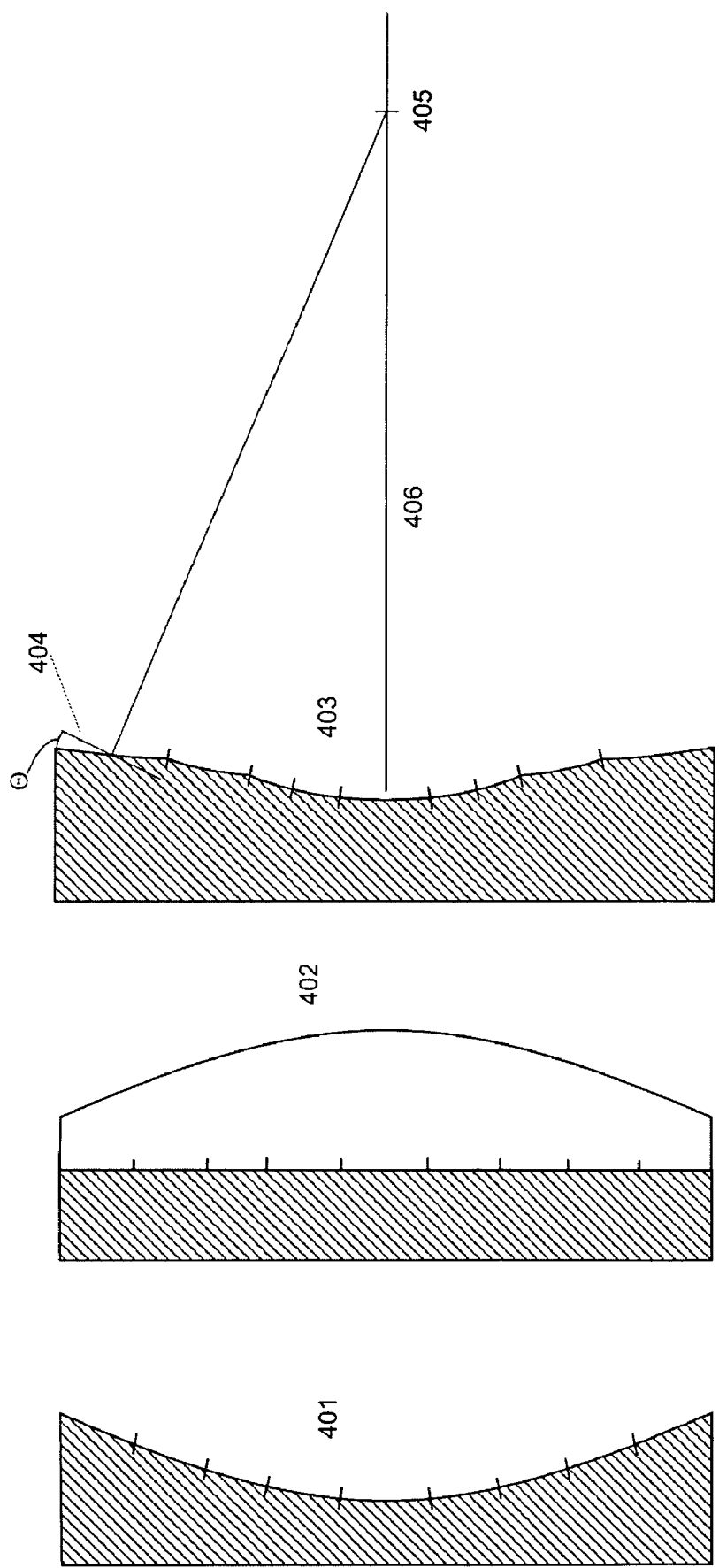
FIG. 4 shows example methods of pre-focusing of the elements in the elevation direction.

FIG. 4c shows an array 403 where the number of elements that participates to the active aperture is increased with depth, as the array in FIG. 3. The elements are then pre-focused at different depths so that the phase error $\theta$ across the element of the front 404 of a wave that originates from the steered focus 405 on the array axis 406, is minimized. One should note that a variable pre-focusing of the elements as in FIG. 4c can also be obtained with a multi-curved lens, or a combination of a multi-curved lens and a multi-curved surface.

There is a requirement on the element width in the elevation direction that the maximum of said phase error is less than a limit $\Theta$. The value of $\Theta$ affects the side-lobe ratio, and the exact value of $\Theta$ depends on the tolerable side-lobe ratio, where $\Theta \sim \pi/2$ is often used as a limit. As the elements with larger distance from the array axis 406 participates to the active aperture only at deeper ranges, the fixed focus depth increases with the element distance from the axis. The width of the elements with deeper focus can then be increased while maintaining said maximal phase error below the limit $\Theta$. Typical elevation pitches of the elements are $\lambda$-$4\lambda$.

It can then be advantageous to increase the element area as a whole number of a base area, as the element impedances will then reduce by this same fixed number, and equal impedance situation for the elements is obtained by parallel coupling of transmitters and receivers for each element according to said number. Equivalently one can increase the transistor areas of the transmitter and receiver amplifiers with said number.

A simplified dynamic elevation focusing of the receive beam can be obtained by starting with a central element that is used for the whole depth range and adding the signal from outer elements in a time sequence, expanding the active aperture with depth, and focusing each element at deeper depths, in a known manner.

For parallel beams in the elevation direction, one must apply different delays to the elevation element signals before the element signals are summed to the RF-signal for each elevation beam direction. The different delays can be introduced in a hierarchical manner, in that the elevation element signals are first delayed for elevation focusing. The element signals are then further delayed for direction steering to the selected elevation beam directions, before they are added to generate the composite RF signal for these directions. For the direct forward elevation direction to the array, there is no added delays before the summation.

When the imaging object has limited movement velocities, one can use synthetic depth focusing of the image beam. We can then use array elements without sub-division in the elevation direction, with a fixed focus in the elevation direction. The synthetic focusing is obtained through a linear combination (linear filtering) of the RF signals from several receive beams with neighboring elevation coordinates and the same azimuth coordinate. The image beam can thus be focused synthetically by post-processing of the received RF-signal as a function of elevation coordinate, to all depths along the image beam and with focal width given by the elevation aperture of the probe. This provides a simple method for elevation focusing for stationary objects, but breaks down when the object moves too fast, like a fetal heart, or the blood.

Hence, while there have shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention. For example, the type and curvature of the array for azimuth scanning could vary from the typical linear phased array to linear switched arrays, and curvilinear switched arrays with different radii of curvature, and combinations thereof. The direction of the rotation axis could also be varied extensively within the scope of the invention.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

We claim:

1. An ultrasound probe for scanning a direction and focus of an ultrasound beam along an azimuth direction and an elevation direction normal to said azimuth direction in a three-dimensional space, comprising:

an ultrasound transducer array for electronic directional scanning and focusing of the ultrasound beam in the azimuth direction within a two-dimensional azimuth plane, said array being mounted to a shaft on a distal end of a rigid elongated device, a handle being disposed at a proximal end of said elongated device, said array being rotatable by a motor arranged in said elongated device or said handle for scanning of the ultrasound beam in said elevation direction through rotation of said array, said elongated device and said array being configured for insertion into a body through one of a vagina, a rectum, and a minimal invasive surgery trocar, and through combined electronic steering of the direction and the focus of the beam in said azimuth direction with mechanical rotation of said array in said elevation direction and with electronic steering of the focus in said elevation direction, directional steering of the beam in a volume region, with electronic steering of the beam focus with depth both in said elevation and said azimuth directions is obtained, and wherein an axis of rotation of the array is at an angle with respect to a longitudinal axis of said elongated device, said angle being greater than zero and less than 70 degrees.

2. The ultrasound probe according to claim 1, wherein the array has a weak convex curvature in the azimuth direction, so that a sector scan with wide near-format is obtained in the azimuth direction by sub-selecting the elements that participate to a particular azimuth beam direction from the total set of elements using electronic switches.

3. The ultrasound probe according to claim 2, wherein a radius of the weak convex curvature is within a range of approximately 100-400$\lambda$.

4. The ultrasound probe according to claim 1, wherein said array having a set of two-dimensional, linearly arranged elements, with a coarse division pitch of the elements in said elevation direction that allows electronic depth steering of the focus in said elevation direction, and a finer division of the elements in said azimuth direction for both electronic scanning of the beam and depth steering of the focus in said azimuth direction within the two-dimensional azimuth plane.

5. The ultrasound probe according to claim 4, wherein the elements in the direction of both the azimuth and elevation are dimensioned such that phase error across the elements is less than 110 degrees for a range in which the elements participate during beam forming.

6. The ultrasound probe according to claim 4, wherein the array elements in the elevation direction are pre-focused, and wherein a pre-focused depth is selected to minimize the phase error across the elements of a wave from the steered focus, throughout the range that the elements participate in the active aperture.

7. The ultrasound probe according to claim 6, wherein the probe includes electronic switches that select and electronically connect electrodes of the elevation elements that participate in the active aperture at any depth, and the switches are steered to increase an active elevation aperture with increasing depth, and the pre-focus of the elements increases with the nearest depth the elements are included in the active elevation aperture so that said phase error in the elevation direction is minimized for the range the elements that participate in the active aperture, and the width of the elements are increased with their pre-focus, so that a maximum value of said phase error is substantially identical for all elements in the range that participate in the active aperture.

8. The ultrasound probe according to claim 6, wherein the elevation width of the elements are selected as a whole number of a base value, so that electric impedance matching to each element is obtained by parallel coupling a number of transmitter/receiver channels to said each element proportional to said whole number for said each element.

9. The ultrasound probe according to claim 4, wherein the probe includes electronic circuits that for each azimuth location select, in the elevation direction, the elements that participate in the active aperture as a function of depth, and delay and sum the elevation element signals from said selected elevation elements to form a composite elevation signal for each azimuth location that is electronically focused in the elevation direction to the origin of the received signal, for electronic selection of a dynamic aperture and focus to focus the receive beam onto the origin of the received signals with depth.

10. The ultrasound probe according to claim 9, wherein the elevation element signals are additionally delayed with multiple delays before being added to multiple composite signals, the composite signals representing multiple parallel beams with small directional differences in the elevation direction.

11. The ultrasound probe according to claim 9, wherein said electronic circuits also select the elevation elements that participate in a transmit aperture and delay transmit pulses for said selected elevation elements to electronically steer the elevation transmit focus.

12. The ultrasound probe according to claim 4, wherein said elements of said array allow angular steering of the beam by an angle of less than 10 degrees in said direction of elevation for at least one of parallel receive and transmit beams in said elevation direction.

13. An ultrasound probe for scanning a direction and focus of an ultrasound beam along an azimuth direction and an elevation direction normal to said azimuth direction in a three-dimensional space, comprising:

an ultrasound transducer array for electronic directional scanning and focusing of the ultrasound beam in the azimuth direction within a two-dimensional plane, said array being mounted to a shaft on a distal end of a rigid elongated device, a handle being disposed at a proximal end of said elongated device, said array being rotatable by a motor arranged in said elongated device or said handle for scanning of the ultrasound beam in said elevation direction through rotation of said array, said elongated device and said array being configured for insertion into a body through one of a vagina, a rectum, and a minimal invasive surgery trocar, and wherein an axis of rotation of the array is at an angle with respect to a longitudinal axis of said elongated device, said angle being greater than zero and less than 70 degrees.

14. The ultrasound probe according to claim 13, wherein the array has a weak convex curvature in the azimuth direction.

15. The ultrasound probe according to claim 14, wherein a radius of the weak convex curvature is within a range of approximately 100-400$\lambda$.

16. An instrument including the ultrasound probe according to claim 13, and means for combining received signals from neighboring beams in the elevation direction with the same azimuth coordinate to provide synthetically focused receive beams.

17. The ultrasound probe according to claim 13, wherein said array having a set of two-dimensional, linearly arranged elements, with a coarse division pitch of the elements in said elevation direction that allows electronic depth steering of the focus in said elevation direction, and a finer division of the elements in said azimuth direction for both electronic scanning of the beam and depth steering of the focus in said azimuth direction within the two-dimensional azimuth plane.

18. The ultrasound probe according to claim 17, wherein the elements in the direction of both the azimuth and elevation are dimensioned such that phase error across the elements is less than 110 degrees for a range in which the elements participate during beam forming.

* * * * *